United States Patent
Gibboney, Jr.

[11] Patent Number: 5,407,637
[45] Date of Patent: Apr. 18, 1995

[54] APPARATUS AND METHOD FOR PRODUCING AN ANTIBIOTIC LIQUID

[75] Inventor: James W. Gibboney, Jr., Conyers, Ga.

[73] Assignee: Scientific Products Corporation, Conyers, Ga.

[21] Appl. No.: 221,107

[22] Filed: Mar. 30, 1994

Related U.S. Application Data

[63] Continuation-in-part of Ser. No. 889,167, May 27, 1992, Pat. No. 5,300,266.

[51] Int. Cl.$^6$ .......................... C01B 13/00; C02F 1/78
[52] U.S. Cl. ............................... 422/22; 422/28; 422/186.07; 423/581; 424/600; 424/613
[58] Field of Search ............ 422/28, 22, 186.07; 423/581; 424/600, 613

[56] References Cited

U.S. PATENT DOCUMENTS

| | | | |
|---|---|---|---|
| 3,005,762 | 10/1961 | Fenn | 422/186 |
| 3,090,745 | 5/1963 | Berghaus | 422/186 |
| 3,332,870 | 7/1967 | Orbach et al. | 422/186 |
| 3,842,286 | 10/1974 | Imris | 250/535 |
| 4,048,668 | 9/1977 | Von Bargen et al. | 361/235 |
| 4,062,748 | 12/1977 | Imris | 204/176 |
| 4,220,545 | 9/1980 | Franzan et al. | 250/530 |
| 4,221,972 | 9/1980 | Oppel et al. | 250/531 |
| 4,417,966 | 11/1983 | Krauss et al. | 204/176 |
| 4,818,355 | 4/1989 | Kanter et al. | 204/170 |
| 4,929,319 | 5/1990 | Dinter et al. | 204/164 |
| 5,002,738 | 3/1991 | Pin et al. | 422/186.13 |
| 5,061,462 | 10/1991 | Suzuki | 422/186.04 |
| 5,098,671 | 3/1992 | Shiota | 422/186.07 |

OTHER PUBLICATIONS

Rice et al., "Handbook of Ozone Technology and Applications", Ann Arbor Science, 1982, pp. 9–25, 105–139.

*Primary Examiner*—Donald P. Walsh
*Assistant Examiner*—Daniel Jenkins
*Attorney, Agent, or Firm*—Michael A. Mann

[57] ABSTRACT

An apparatus and method for producing an antibiotic liquid. The apparatus includes an ion generator that produces negatively-charged molecules of the formula $[MO_x]^-$, where M is a positive ion, O is oxygen and x is a number at least equal to 3, and means for mixing a gas containing said molecules with a liquid such as water. Molecules $[MO_x]^-$ are produced in a generator that comprises a specially shaped anode and cathode spaced apart from each other in a non-conducting housing. When a substantially constant voltage is applied across the anode and cathode, a plasma forms between and around them that in turn forms a magnetic field around the plasma and the anode. Diatomic oxygen molecules enter the housing and are polarized by the magnetic field and the resulting oxygen ions accelerated toward the plasma. The plasma excites and confines the oxygen ions long enough for them to strike the materials forming the cathode and anode, releasing positive ions of the cathode and anode materials which bind together and form charged molecules $[MO_x]^-$. Upon exiting the generator, air enriched with the charged molecules is mixed with water to produce a liquid having antibiotic properties.

20 Claims, 4 Drawing Sheets

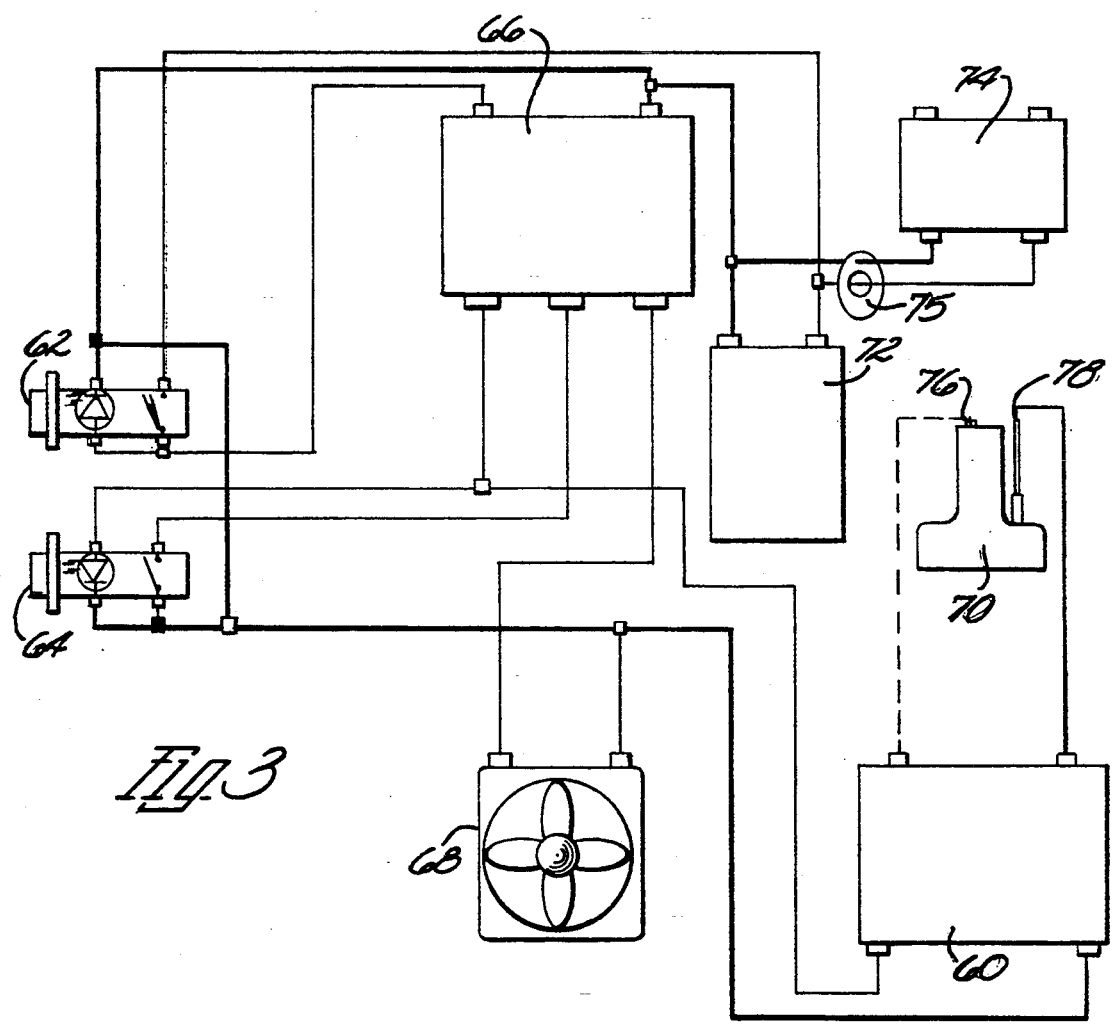

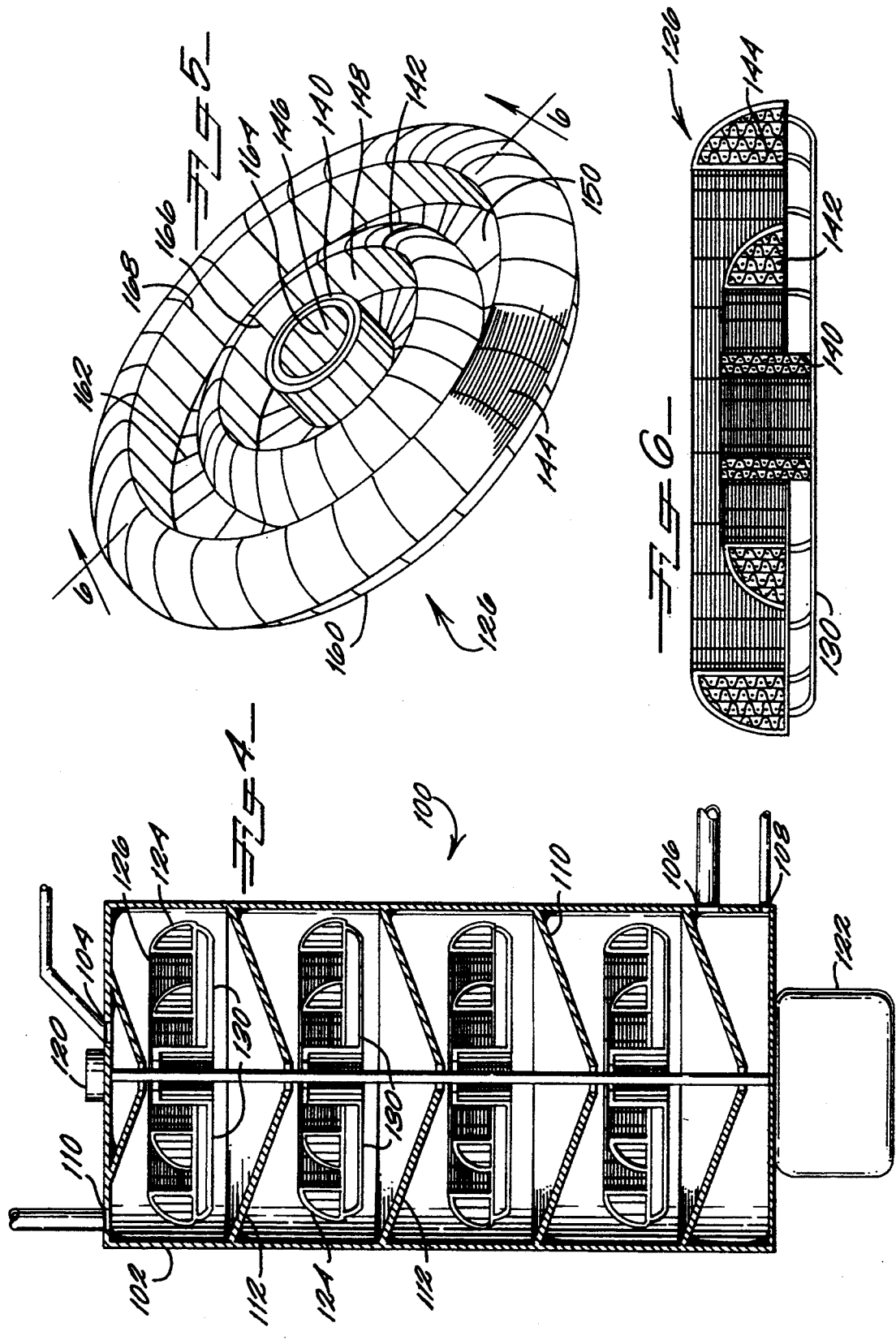

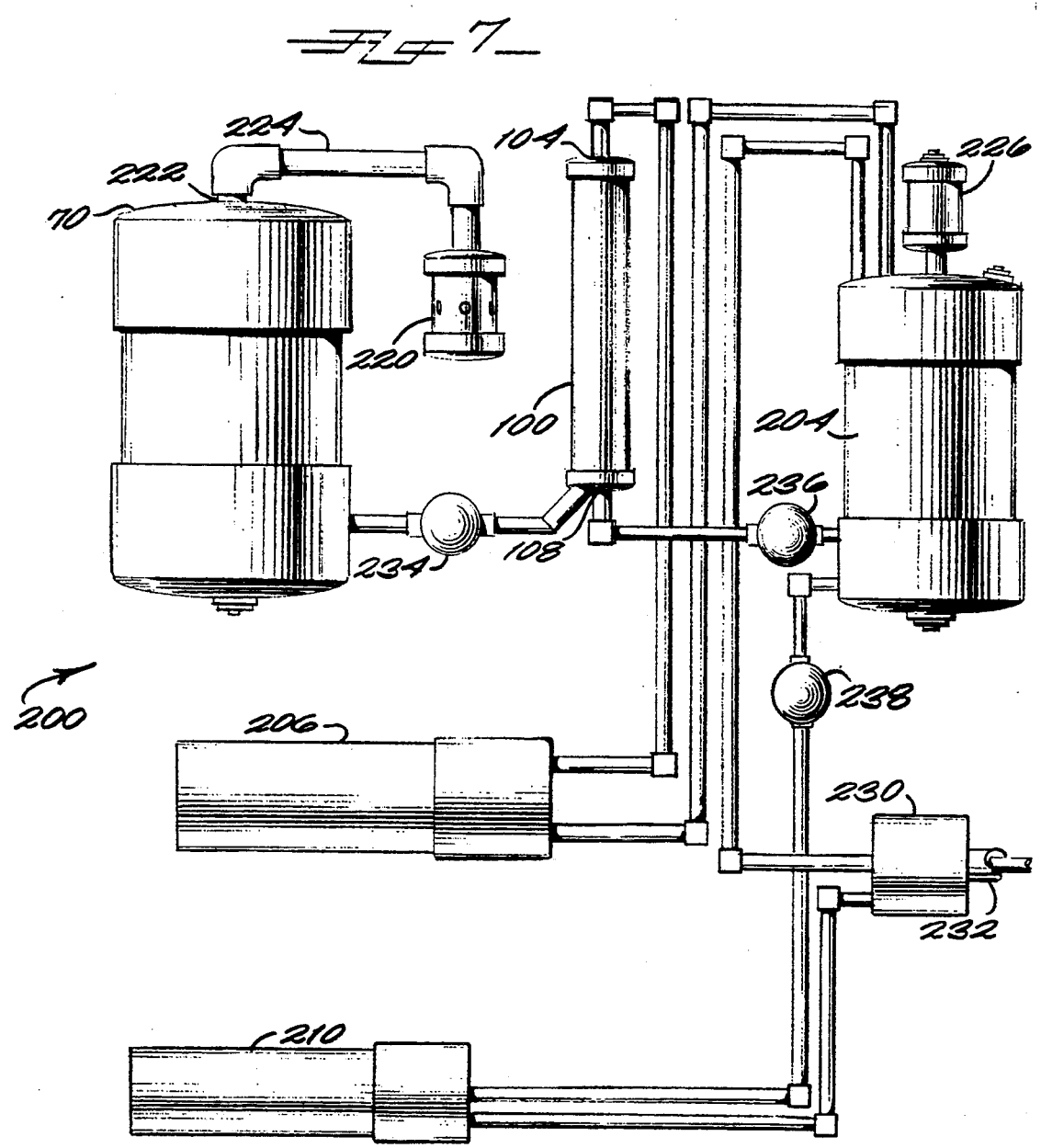

APPARATUS AND METHOD FOR PRODUCING AN ANTIBIOTIC LIQUID

BACKGROUND OF THE INVENTION

1. Field of the Invention

This application is a continuation-in-part of application Ser. No. 07/889,167, filed May 27, 1992, now U.S. Pat. No. 5,300,266.

The present invention relates to an apparatus and method for producing an antibiotic liquid. In particular, the present invention relates to methods and apparatus for generating, using DC current, negatively charged molecules of the form $[MO_x]-$, where M is a positive ion, O is oxygen, and x is a number at least equal to 3, and adding said molecules to a liquid such as water to form a mixture having antibiotic properties.

2. Discussion of Background

Water for industrial and household use can be purified by a variety of processes including filtration, distillation, chlorination, and bioremediation which uses microorganisms to oxidize pollutants. Large-scale purification systems designed for municipal water supplies produce safe, potable water in an efficient and cost-effective manner. However, water from a municipal system may contain small amounts of heavy metals, hydrocarbons and other pollutants that affect its taste and quality. Therefore, manufacturers and processors of foods, drugs, medical supplies, silicon microchips, etc. frequently require higher-purity water to ensure the quality of their products. In addition, many homeowners install water purification apparatus to treat swimming pools, or to purify well water or municipal water. Apparatus for these types of uses is inefficient and expensive, and, in the case of manufactured goods, adds to the cost of the product.

It is well known that water can be purified and disinfected by aeration, that is, by introducing air into the water to oxidize and remove impurities. The term "aerate" as used herein means to introduce air or some other gas into a liquid by spraying, bubbling, stirring or any other convenient method; the term "aerated" refers to a liquid that contains fine bubbles of air or other gas. Aeration can be accomplished by bubbling air through the water, or by spraying or stirring the water to allow contact with atmospheric air. The greater the surface area of exposed liquid, the more efficient the aeration process, thus, the water may be atomized to produce small droplets and thereby maximize the surface area. Aeration may be conducted with ambient air, oxygen-enriched air, ozone-enriched air of some other gas that has the desired antibiotic properties.

Ozone is recognized as a substance that can be used for oxidizing many substances and also for disinfecting, deodorizing and sanitizing because ozone reacts with water to form hydrogen peroxide, a well known antibiotic. Industrial demand for ozone as an oxidant is strong. Ozone and other disinfectants, deodorants and sanitizers, such as household cleansers, detergents, sprays, air fresheners, air filters, and the like, have a great many applications for industrial, business and private use.

A number of ozone generators exist, most of them operating on alternating current. There are two known to use direct current, that is, a current that does not change polarity, namely, those described in U.S. Pat. No. 4,417,966 issued to Krauss, et al. and in U.S. Pat. No. 4,048,668 issued to Von Bargen et al, but these both use a time-varying current level. The former patent describes a device with a current chopped at a frequency of about 350 Hz; the latter describes a pulsed current having a frequency of 10 kHz to 16 kHz. Presently-available ozone generators require cooling mechanisms to dissipate the quantities of heat produced in the generation of ozone, or systems that operate at an elevated pressure, and thus, are not suitable for use outside the industrial environment, in particular, these types of ozone generators are not suitable for aerating water.

There is a need for a water-treatment apparatus that is simple and reliable to operate. In particular, there is a need for an apparatus that can treat water quickly, completely, and effectively and do so without the inconvenience associated with presently-available systems.

SUMMARY OF THE INVENTION

According to its major aspects and broadly stated, the present application is an apparatus for producing an antibiotic liquid. The apparatus includes an ion generator that produces negatively-charged molecules of the formula $[MO_x]-$, where M is a positive ion, O is oxygen and x is a number at least equal to 3, and means for mixing the molecules with a liquid such as water. Upon exiting the generator, air enriched with the charged molecules is mixed with water or some other liquid to produce a potable liquid that is also suitable for use in deodorizing, sanitizing and disinfecting.

The ion generator is an important feature of the present invention. The ion generator includes a specially shaped anode and cathode spaced apart from each other in a non-conducting housing. When a substantially constant voltage is applied across the anode and cathode, a plasma forms between and around them which in turn forms a magnetic field around the plasma and the anode. Diatomic oxygen molecules enter the housing and are polarized by the magnetic field and the resulting oxygen ions accelerate toward the plasma. The plasma excites and confines the oxygen ions long enough for them to strike the materials forming the cathode and anode, releasing positive ions of the cathode and anode materials which bind together and form the negatively-charged molecules $[MO_x]-$.

Another important feature of the present invention is the negatively-charged molecules produced by the ion generator. The liquid produced by the apparatus has antibiotic properties and thus, the negatively-charged molecules are effective against molds, fungi, mildew and bacteria.

Still another feature of the present invention is the adjustability of the generator and the concentration of negatively-charged molecules in the air or gas supplied to the mixing means. The gap between the anode and cathode of the generator can be increased or decreased, and a resistor, preferably an adjustable resistor, is carried by the cathode so that the intensity of the plasma field can be changed or adjusted to control the output. In addition, a valve at the outlet of the generator can be adjusted to control the admixture of negatively-charged molecules with the air that is input to the mixing means.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 3 is a schematic showing an ion generator according to a preferred embodiment of the present invention in a complete system;

FIG. 4 is a cross-sectional view of an apparatus for aerating water according to a preferred embodiment of the present invention;

FIG. 5 is a perspective view of the atomizer of FIG. 4;

FIG. 6 is a cross-sectional view of the atomizer of FIG. 4; and

FIG. 7 shows a system for producing an antibiotic liquid according to a preferred embodiment of the present invention.

DETAILED DESCRIPTION OF A PREFERRED EMBODIMENT

The present invention is an apparatus and method for producing an antibiotic liquid. The liquid, preferably water, contains negatively-charged molecules that oxidize, and thereby destroy, bacteria, mold, fungus, mildew, and odors. The molecules are of the form $[MO_x]^-$, where M is a positive ion, O is oxygen, and x is a number having a value at least equal to three. In particular, x will equal three, four, or five. Once the liquid is in contact with a surface, be it a wall, a carpet fiber, a dust particle or a microorganism, the charge on the particle is quickly neutralized and the excess oxygens oxidize aggressively all around it. Water or water vapor is converted to hydrogen peroxide, an effective antiseptic itself.

Figure 1:
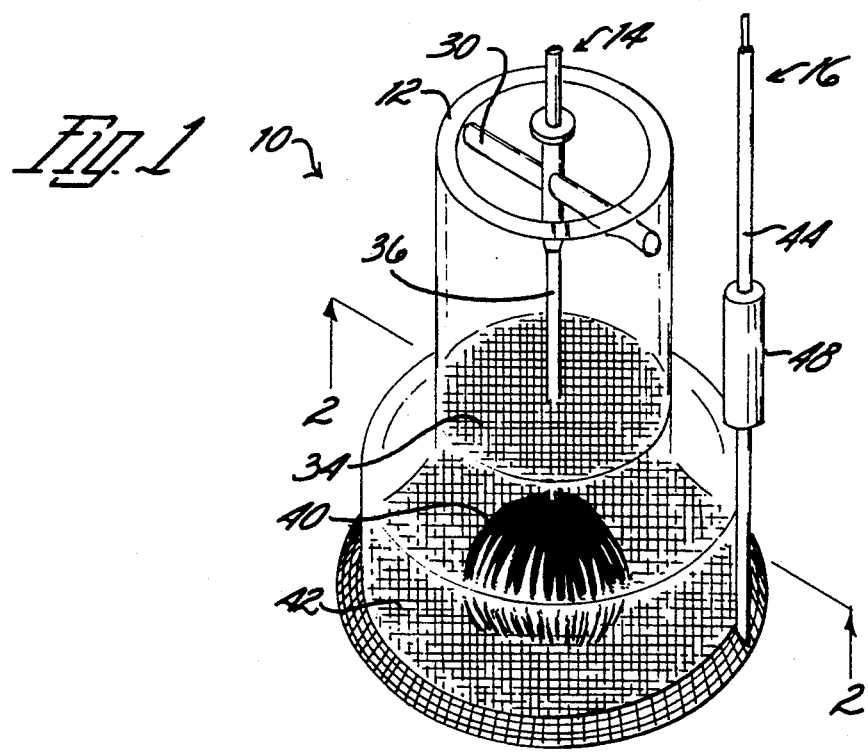
FIG. 1 is a perspective view of an ion generator according to a preferred embodiment of the present invention.
Figure 2:
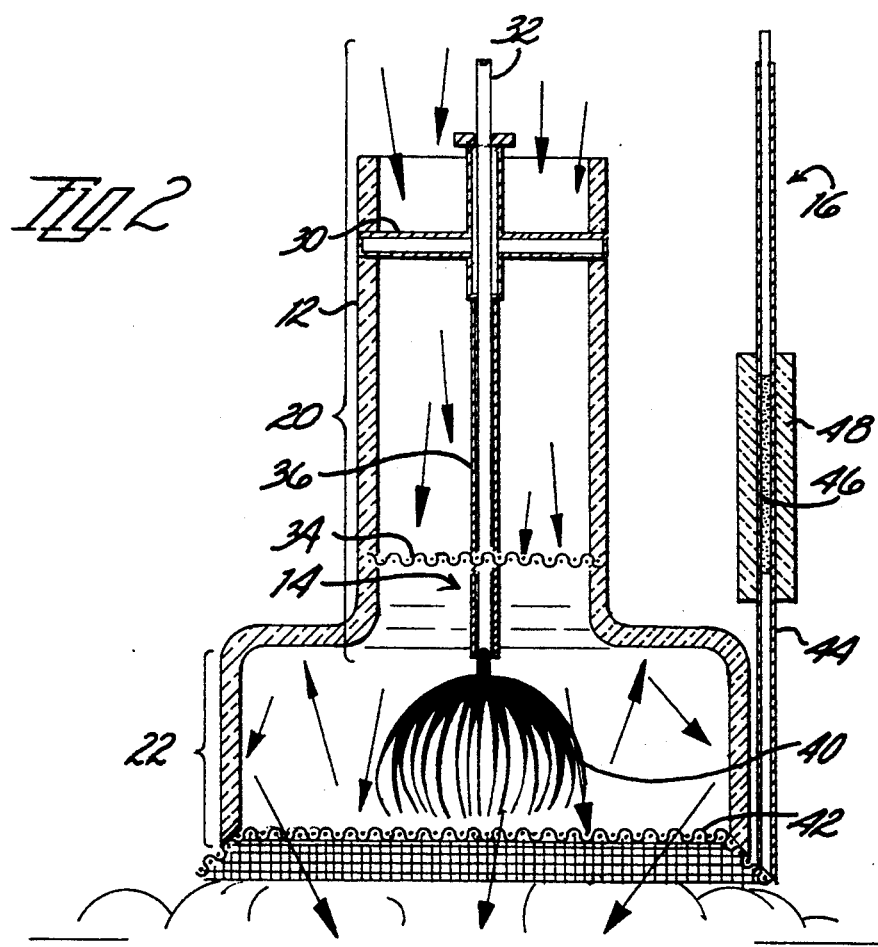
FIG. 2 is a side cross section of the ion generator as shown in FIG. 1 taken along line 2—2.

Referring now to FIGS. 1 and 2, there is illustrated an apparatus for generating charged molecules according to a preferred embodiment of the present invention. The apparatus, generally indicated by the reference character 10, comprises a housing 12 made of a non-conducting, preferably insulating material, such as glass. Inside is an anode 14. On the end is a cathode 16. Anode 14 has two major portions: a first portion 20 for generating a long electric field; and a second portion 22 for generating a plasma field. The electric field and plasma field generate a magnetic field that pulls diatomic oxygen molecules apart, and accelerates them toward the plasma and ultimately out of apparatus 10.

First portion 20 comprises a stator bar 30, an anode adjustment shaft 32, a grid 34, and an anode generator shaft 36, all at the same electrical potential. Stator bar 30 provides support for anode 14. Shaft 36 is relatively long so as to produce an elongated electric field in order to create and maintain a high level of ionization of the molecules passing through housing 12. Shaft 36 also acts as a stator to the anode adjustment shaft 32. When a substantially constant voltage is applied across anode 14 and cathode 16, the electrical field thus established along anode generator shaft 36 from stator bar 30 to grid 34 generates a magnetic field oriented so that diatomic oxygen molecules entering housing 12 at 18 will be ionized and accelerated parallel to shaft 36. A voltage of approximately 20 KV is sufficient to generate the magnetic and plasma fields. Housing 12 maintains the oxygen ions, and other ions, at a high state of excitation as they continue through apparatus 10.

Second portion 22 of anode 14 cooperates with cathode 16 in establishing the plasma field. Second portion 22 comprises a plurality of electrodes 40 that flare outwardly from a common attachment to anode adjustment shaft 32. Electrodes 40 are wider at one end, the end where they are in electrical and physical attachment with each other and adjustment shaft 32, and taper toward the opposing end, where they are narrower and separated. Alternatively, electrodes 40 can be interwoven, or in some other configuration, so long as they are separated from each other at the end nearer to cathode 16. The magnetic field encloses the plasma field and assists in the escape of the charged molecules from the confining plasma field.

Cathode 16 is in the form of a grid 42 and a cathode conductor 44 with a cathode resistor 46 and resistor housing 48. Grid 42 can also be in the form of a mesh or perforated plate, so long as it has a plurality of through-holes through which charged molecules, indicated by arrows in FIG. 2, can pass.

Anode adjustment shaft 32 threadedly engages anode generator shaft 36 and has a slot 50 at the end so that, by turning shaft 32, it can be advanced or withdrawn to adjust the size of the gap between anode and cathode 16. An adjustable anode shaft 32 having approximately 32 turns per inch allows sufficient fineness of control for selecting a suitable gap spacing.

Cathode 16 has resistor 46 located within resistor housing 48 of cathode conductor 44 to load cathode 16 and thereby set the intensity of the plasma. If the voltage is 20 KV, the current through apparatus 10 is preferably approximately 250 μamps, which produces negligible heat. A fan may optionally be used to drive air from the anode side to increase throughput, but is not required because the magnetic field supplies sufficient pressure through the acceleration of the oxygen ions. Thus, no cooling or other special treatment of the incoming air is required in order to produce the charged molecules.

Anode 14 is a "sacrificial anode," that is, the material of anode 14 is consumed during operation of apparatus 10 so that the anode must eventually be replaced. Anode 14 and cathode 16 are preferably made of two different conducting materials, preferably soft, electron-rich materials so that their positive ions can be released by the incident oxygen ions. Soft metals, carbon, fiberglass, or other conductors and semi-conductors are examples of electrode materials that will be satisfactory. In particular, anode 14 could be made of bronze and cathode 16 of aluminum. However, there needs to be a source of positive ions and there needs to be an anode and a cathode. The present apparatus combines these requirements in an anode and cathode made of conductor materials that will release positive ions when struck by oxygen ions accelerated by the magnetic field.

In use, as illustrated in FIG. 3, an generator electronic module 60 is activated by two switches 62, 64. Switch 62 is a main power switch which activates a control electronics module 66 and a fan 68. Switch 64 is preferably a "momentary" switch, that is, it does not remain in the "on" position. Switch 64 signals control electronics module 66 to activate generator electronics module 60 which in turn activates apparatus 70. Apparatus 70 is preferably operated continuously. However, apparatus 70 may be turned off by generator electronics module 60 after a preselected period of time if desired. Fan 68 may remain on for a while longer to purge the system.

Power is supplied either by a battery 72 or a standard source of 120 VAC 74 rectified by a rectifier 75.

Generator electronics module 60 generates a high voltage, preferably about 20 KV, which is applied across anode 76 and cathode 78 of apparatus 70. Anode 76 and cathode 78 generate a high-density electrical field which in turn generates a high density plasma field around and between anode 76 and cathode 78, which in turn generates a high density magnetic field inside apparatus 70. The magnetic field encloses and encapsulates the plasma field and runs the length of the electrical field. The magnetic field polarizes the incoming diatomic oxygen molecules, which are then separated into oxygen ions by magnetic repulsion, electrical excitation and high velocity molecular collisions. The magnetic field accelerates the oxygen ions toward anode 76 and cathode 78. The oxygen ions strike anode 76 and cathode 78, causing positive ions from the anode and cathode conductor material to be released. In the plasma, these ions reach a high level of excitation and the number of excitation collision coincidences. The oxygen ions bond with each other and with ions released from anode 76 and cathode 78 to form negatively-charged, triatomic, quadratomic, and quintatomic molecules of the form $[MO_x]^-$ where M is a positive ion, O is oxygen and x is a number at least equal to 3. These molecules, having more momentum than the individual oxygen ions, escape the plasma and charge toward cathode 78. The charged molecule will pass through holes in cathode 78 and exit apparatus 70.

The materials used for anode 76 and cathode 78 determine the activity level of the negatively-charged molecules $[MO_x]^-$, the distance traveled by the molecules, and the lifetime of the molecules. Ozone ($O_3$), for example, is neutral with an average lifetime of approximately 8 hours. A charged molecule formed by apparatus 70 typically has an average lifetime that depends on the time that elapses before the molecule collides with another molecule or a surface. The molecules neutralize within a few seconds of striking a surface. Because of their high velocity, and ionic attraction between the negatively-charged molecules and the net positive charge on many types of surfaces, the molecules produced by apparatus 70 act as though they were lighter than air.

Upon leaving apparatus, the charged molecules $[MO_x]^-$ adhere to and penetrate nearby surfaces. There, the charge is quickly neutralized as the polyatomic oxygen ($O_x$, where $x \geq 3$) decomposes to diatomic oxygen ($O_2$), which in turn oxidizes bacteria, fungus, mold, and mildew on those surfaces.

Cultures of three common resistant microorganisms showed substantially reduced growth when exposed to negatively-charged molecules produced by the apparatus. Test results showed that growth of exposed cultures was reduced by as much as 99.8% when compared to control cultures, with the degree of reduction depending on the exposure time. Tests were performed on porous and hard surfaces (porcelain, stainless steel, glass, glass fiber paper), and under wet and dry conditions. The organisms tested included *Staphylococcus aureus* (resistant to drying), *Klebsiella pneumonia* (resistant to aqueous disinfectants), and *Bacillus subtilis* (resistant to drying and disinfectants).

Referring now to FIG. 4, there is shown an apparatus for producing a liquid antibiotic according to a preferred embodiment of the present invention. Apparatus 100 includes a housing 102 with a liquid inlet 104, a gas inlet 106, a liquid outlet 108, and a gas outlet 110. Housing 102 contains a plurality of funnels 112.

A shaft 120 extends through housing 102, powered by a drive unit 122. A plurality of fan blade assemblies 124 are mounted on shaft 120, with each assembly holding an atomizer disc 126 (to be described below). Each assembly 124 has a plurality of fan blades 130 attached thereto, generally as indicated in FIG. 4.

In operation, water or some other suitable liquid enters housing 102 at inlet 104 and is funneled downwards by the uppermost of funnels 112. A gas, preferably an oxygen-containing gas such as air, and most preferably air enriched with negatively-charged molecules produced by apparatus 70, enters housing 102 at gas inlet 106 and is guided upwards by fan blades 130. At least a portion of the gas is mixed with the liquid; unabsorbed gas exits housing 102 at outlet 110.

As the gas moves from inlet 106 to outlet 110, spinning blades 130 force the gas through each successive atomizer disc 126, thereby producing vortices under the next highest funnel 112, creating an efficient mixing action with the liquid flowing from inlet 104 towards outlet 108. Some of the liquid is vaporized and condenses on the surfaces of funnels 112. Vapor condensed on each funnel 112 is funneled to the next funnel, where it mixes with gas flowing in the opposite direction. The amount of gas mixed with the liquid exiting housing 102 at outlet 108 depends on the rate of rotation of shaft 120, the number of funnels 112 and blade assemblies 124, the structure of atomizer discs 126, and the rate of flow of gas and water into inlets 106 and 104, respectively.

An atomizer disc 126 suitable for use with the invention is shown in FIGS. 5 and 6. Disc 126 consists of a free screen mesh, made of any of a number of suitable materials including aluminum and stainless steel. Disc 126 includes three mesh sections 140, 142, 144, with a central hole 146 for mounting on shaft 120. Gaps 148, 150 separate sections 140 and 142, and sections 142 and 144, respectively. The lower surface 160 of disc 126 has a plurality of radial supporting wires 162 extending from inner section 140 to outer section 144. Sections 140, 142, 144 may also be supported by wires 164, 166, 168, respectively.

Water (or some other liquid) first enters disc 126 at hole 146. As disc 126 rotates, the water strikes the mesh of inner section 140 and is atomized into small droplets on the order of 10–20 microns in size. The droplets are driven through the mesh and traverse gap 148 between inner section 140 and center section 142. In gap 148, the droplets are mixed with gas driven upwards from inlet 106 by rotating fan blades 130. Formation of vortexes in gap 148 promotes mixing of the water droplets with the gas. The mixture passes through center section 142, where the water droplets are further reduced in size (to approximately 5–10 microns) and pass into gap 150 where further mixing with upwardly-moving gas occurs. Finally, the gas-water mixture passes through the mesh of outermost section 144, where the water droplets are reduced to approximately 1–2 microns in size. The mixture of atomized water droplets and gas strikes the surface of funnel 112, which funnels the mixture downwards to the next disc 126 where the above-described cycle is repeated.

The size of the water droplets produced by each disc 126 depends on the speed of rotation of shaft 120, the dimensions of discs 126, and the mesh size of the material of the discs. Preferably, these parameters are adjusted so that the water droplets exiting disc 126 are approximately 1-2 microns in size, however smaller or larger water droplets may also be useful.

Innermost section 140 preferably has at least two layers of mesh (as shown in FIGS. 5 and 6), however, section 140 may contain a single layer, or more than two layers without departing from the spirit of the invention. Similarly, sections 142 and 144 may each have a single mesh layer as shown, or a plurality of layers. Discs 126 having three mesh sections (140, 142, 144) are shown, however, a different number of such sections may be used if desired.

An apparatus 200 for producing an antibiotic liquid according to a preferred embodiment of the present invention is shown in FIG. 7. Apparatus 200 includes an ion generator such as generator 70, a mixing apparatus such as apparatus 100, a reservoir 204, a mixing pump 206 and a circulating pump 210, connected generally as shown. Apparatus 70 may include a filter and shutter valve assembly 220, connected to an inlet 222 by a conduit 224.

Air enters apparatus 70, where at least a portion of the diatomic oxygen molecules in the air are ionized and form negatively-charged molecules (ions) of the form $[MO_x]^-$. The ion-enriched air is transferred to apparatus 100, where the air is mixed with water (or other suitable liquid) supplied by pump 206 to inlet 104. Aerated water exits apparatus 100 at outlet 108 and is transferred to reservoir 204. Gas (including ions supplied by apparatus 70) is vented by a vent 226. The treated water in reservoir 204 may be recirculated through apparatus 100 to maintain the level of aeration of the water, generally as indicated in FIG. 7.

Water—or other liquid—treated by apparatus 200 has antibiotic properties due to the negatively-charged molecules mixed with the water. The molecules mix well with water in above-described apparatus 200 to produce an effective, non-selective antibiotic liquid. As described above, the molecules substantially retard growth of common varieties of microorganisms, including molds, mildews., fungus, and bacteria. The mixture remains active even when used in ultrasonic apparatus.

The negatively-charged molecules produced by apparatus 70 are richer in atomic oxygen than air, since the molecules contain polyatomic oxygen ($O_x$, where $x \geqq 3$) rather than diatomic oxygen ($O_2$). Therefore, the aerated liquid produced by apparatus 200 contains more oxygen than a liquid mixed with atmospheric air. The concentration of negatively-charged molecules $[MO_x]^-$ in the treated water depends on the components and operating conditions of apparatus 200, including the anode and cathode materials of apparatus 70, the configuration of apparatus 100, and the operating speed of pump 200.

Air containing approximately 60 ppm ozone was bubbled into a first container of water until the ozone concentration of gas exhausted from the water reached 30 ppm. Similarly, air containing approximately 60 ppm of molecules $[MO_x]^-$ from apparatus 70 was bubbled into second water container until the $[MO_x]^-$ concentration of gas was 30 ppm. At this point, the treated water in the second container had several times the dissolved oxygen concentration of the ozone-containing water in the first container. A zinc tab was placed in each container. After approximately 20 minutes, the tab in the second container had mostly dissolved and oxidized, whereas the tab in the ozone-containing water showed only a slight dulling of the surface due to light oxidation.

Liquid may be pumped from reservoir 204 to the target site for use. For example, as shown in FIG. 7, treated water from reservoir 204 may be pumped to an adapter 230 and a double hose 232 for use in, for example, the irrigation of a surgical wound, as shown in FIG. 7. The concentration of negatively-charged molecules in the liquid, and the flow rate of the liquid throughout apparatus 200, may be controlled by flow valves 234, 236, 238. The liquid, containing negatively-charged molecules produced in apparatus 70, continuously disinfects the site without the foaming effect produced by hydrogen peroxide. Water treated according to the invention may be used wherever bacterial and viral infection control is desired, for example, as an antibiotic hand and body wash for medical personnel including physicians, dentists, nurses, etc., and a hand wash for restaurant workers and others in the food service industry. Other applications include treatment of swimming pool water and well water, and wash downs of equipment in food processing plants and retail outlets (supermarkets, butcher shops and so forth). Water treated according to the invention may be used to wash food products, for example, to rinse meat in order to destroy salmonella and other bacteria. In addition, water treated in apparatus 200 is potable since most heavy metals such as cerium, cadmium, mercury, lead and nickel, as well as hydrocarbons, carbon tetrachloride, ammonia, hydrogen cyanide, nitrogen, and other pollutants common to water table pollution from land fill leachate are removed.

It will be apparent to those skilled in the art that many changes and substitutions can be made to the preferred embodiment herein described without departing from the spirit and scope of the present invention as defined by the appended claims.

What is claimed is:

1. A method for making an antibiotic liquid, said method comprising the steps of:

producing charged molecules of the form $[MO_x]^-$, where M is a positive ion of an electrically conducting material, O is oxygen, and x is a number at least equal to 3, said molecules being useful as an antibiotic; and mixing said molecules with a liquid.

2. The method as recited in claim 1, wherein said molecules are made from diatomic oxygen, and wherein said producing step further comprises:

forming a plasma field;

separating said diatomic oxygen into oxygen ions;

accelerating said oxygen ions toward said plasma field;

confining said oxygen ions in said plasma field where said electrically conducting material is located so that said oxygen ions strike said electrically conducting materials, releasing said positive ions from said material, whereby at least a portion of said oxygen ions become bound to said positive ions to form said charged molecules that can escape said plasma.

3. The method as recited in claim 1, wherein said molecules are made from diatomic oxygen, wherein said mixing step further comprises:

directing said molecules in a first direction; and directing said liquid in a second direction substantially opposite to said first direction so that said molecules and said liquid mix.

4. The method as recited in claim 1, further comprising the initial step of producing droplets of said liquid.

5. The method as recited in claim 2, wherein said forming step further comprises the steps of:
providing an anode and a cathode, said anode separated from said cathode by a gap, said anode comprising a plurality of electrodes attached together at one end and separated at an opposing end, said opposing end oriented toward said cathode; and
applying a substantially constant voltage between said anode and said cathode.

6. The method as recited in claim 2, wherein said accelerating step further comprises the steps of:
establishing a magnetic field; and
orienting said magnetic field so that said oxygen ions accelerate toward said plasma field.

7. The method as recited in claim 1, wherein said forming step further comprises the steps of:
providing an anode and a cathode, said anode separated from said cathode by a gap, said anode comprising a plurality of electrodes attached together at one end and separated at an opposing end, said opposing end oriented toward said cathode; and
applying a direct electrical current between said anode and said cathode.

8. The method as recited in claim 1, wherein said separating step further comprises the steps of:
forming a magnetic field; and
polarizing said diatomic oxygen in said magnetic field.

9. The method as recited in claim 1, further comprising the step of mixing said molecules with a gas.

10. The method as recited in claim 1, wherein said liquid is water, and wherein said method further comprises the step of mixing said molecules with air.

11. The method as recited in claim 1, wherein said molecules are made from diatomic oxygen, and wherein said producing step further comprises the steps of:
providing an anode and a cathode made of different electrically conducting materials, said anode separated from said cathode by a gap, said anode comprising a plurality of electrodes attached together at one end and separated at an opposing end, said opposing end oriented toward said cathode;
applying a substantially constant voltage between said anode and said cathode to form a plasma field therebetween;
separating said diatomic oxygen into oxygen ions;
accelerating said oxygen ions toward said plasma field; and
confining said oxygen ions in said plasma field so that said oxygen ions strike said anode and said cathode, releasing said positive ions from said anode and said cathode, whereby at least a portion of said oxygen ions become bound to said positive ions to form said charged molecules.

12. The method as recited in claim 1, wherein said molecules are made from diatomic oxygen, and wherein said producing step further comprises the steps of:
providing an anode and a cathode made of different electrically conducting materials, said anode separated from said cathode by a gap, said anode comprising a plurality of electrodes attached together at one end and separated at an opposing end, said opposing end oriented toward said cathode;
applying a direct electrical current between said anode and said cathode to form a plasma field therebetween;
separating said diatomic oxygen into oxygen ions;
accelerating said oxygen ions toward said plasma field; and
confining said oxygen ions in said plasma field so that said oxygen ions strike said anode and said cathode, releasing said positive ions from said anode and said cathode, whereby at least a portion of said oxygen ions become bound to said positive ions to form said charged molecules.

13. A method for making an antibiotic liquid, said method comprising the steps of:
providing an anode and a cathode, said anode having a first portion and an adjacent second portion, said first portion shaped to form a magnetic field between said anode and said cathode when a direct electrical current is applied across said anode and said cathode, said magnetic field oriented to accelerate ions from said first portion toward said second portion, said second portion shaped to form a plasma between said second portion and said cathode when said electrical current is applied across said anode and said cathode;
applying a direct electrical current between said anode and said cathode to form said magnetic field and said plasma field;
separating diatomic oxygen into oxygen ions in said magnetic field;
accelerating said oxygen ions toward said plasma field;
confining said oxygen ions in said plasma field so that said oxygen ions strike said anode and said cathode, releasing positive ions having the formula M from said anode and said cathode, whereby at least a portion of said oxygen ions become bound to said positive ions to form charged molecules having the formula $[MO_x]^-$, where O is oxygen, and x is a number $\geq 3$; and
mixing said charged molecules with a liquid.

14. The method as recited in claim 13, wherein said mixing step further comprises:
directing said molecules in a first direction; and
directing said liquid in a second direction substantially opposite to said first direction so that said molecules and said liquid mix.

15. The method as recited in claim 13, further comprising the initial step of producing droplets of said liquid.

16. The method as recited in claim 13, wherein said providing step further comprises providing an anode and a cathode made of different electrically conducting materials.

17. The method as recited in claim 13, wherein said providing step further comprises providing an anode made of bronze and a cathode made of aluminum.

18. The method as recited in claim 13, wherein said providing step further comprises providing an anode and a cathode made of electron-rich materials.

19. The method as recited in claim 13, wherein said liquid is water, and wherein said method further comprises the step of mixing said molecules with air.

20. The method as recited in claim 13, further comprising the initial step of producing droplets of said liquid, wherein said mixing step further comprises:
directing said molecules in a first direction; and
directing said droplets in a second direction substantially opposite to said first direction so that said molecules and said droplets mix.

* * * * *